United States Patent [19]

Rocklin

[11] Patent Number: 4,751,189
[45] Date of Patent: Jun. 14, 1988

[54] METHOD FOR BALANCING BACKGROUND CONDUCTIVITY FOR ION CHROMATOGRAPHY

[75] Inventor: Roy D. Rocklin, Sunnyvale, Calif.
[73] Assignee: Dionex Corporation, Sunnyvale, Calif.
[21] Appl. No.: 838,512
[22] Filed: Mar. 11, 1986
[51] Int. Cl.[4] ...................... B01D 15/08; G01N 30/02
[52] U.S. Cl. .................................... 436/150; 436/161; 436/178; 204/182.3; 204/301; 210/656
[58] Field of Search ...................... 210/656, 659, 198.2; 422/70; 436/161, 150, 100, 182; 204/301, 182.3, 182.4, 182.5

[56] References Cited

U.S. PATENT DOCUMENTS 4,500,431 2/1985 Miyanaga et al. .................. 210/656
4,507,390 3/1985 Horiuchi et al. ............... 210/656 X

*Primary Examiner*—John F. Niebling
*Assistant Examiner*—John S. Starsiak, Jr.
*Attorney, Agent, or Firm*—Flehr, Hohbach, Test, Albritton & Herbert

[57] ABSTRACT

A method of ion chromatography in which the sample passes through a chromatographic column, a suppressor, and a conductivity detector, using a gradient electrolyte eluent. A non-ionic polyhydroxy compound is added with the eluent to the chromatographic column at a concentration inversely related to the concentration of the electrolyte which increases with time. The effluent is passed through a membrane suppressor for the conductivity of the electrolyte. The regenerant stream in the suppressor includes a complexing agent (boric acid) which passes through the membrane into the effluent to form highly ionized complex which counterbalances the increased background conductivity of the electrolyte to stabilize the background conductivity in the conductor.

7 Claims, 2 Drawing Sheets

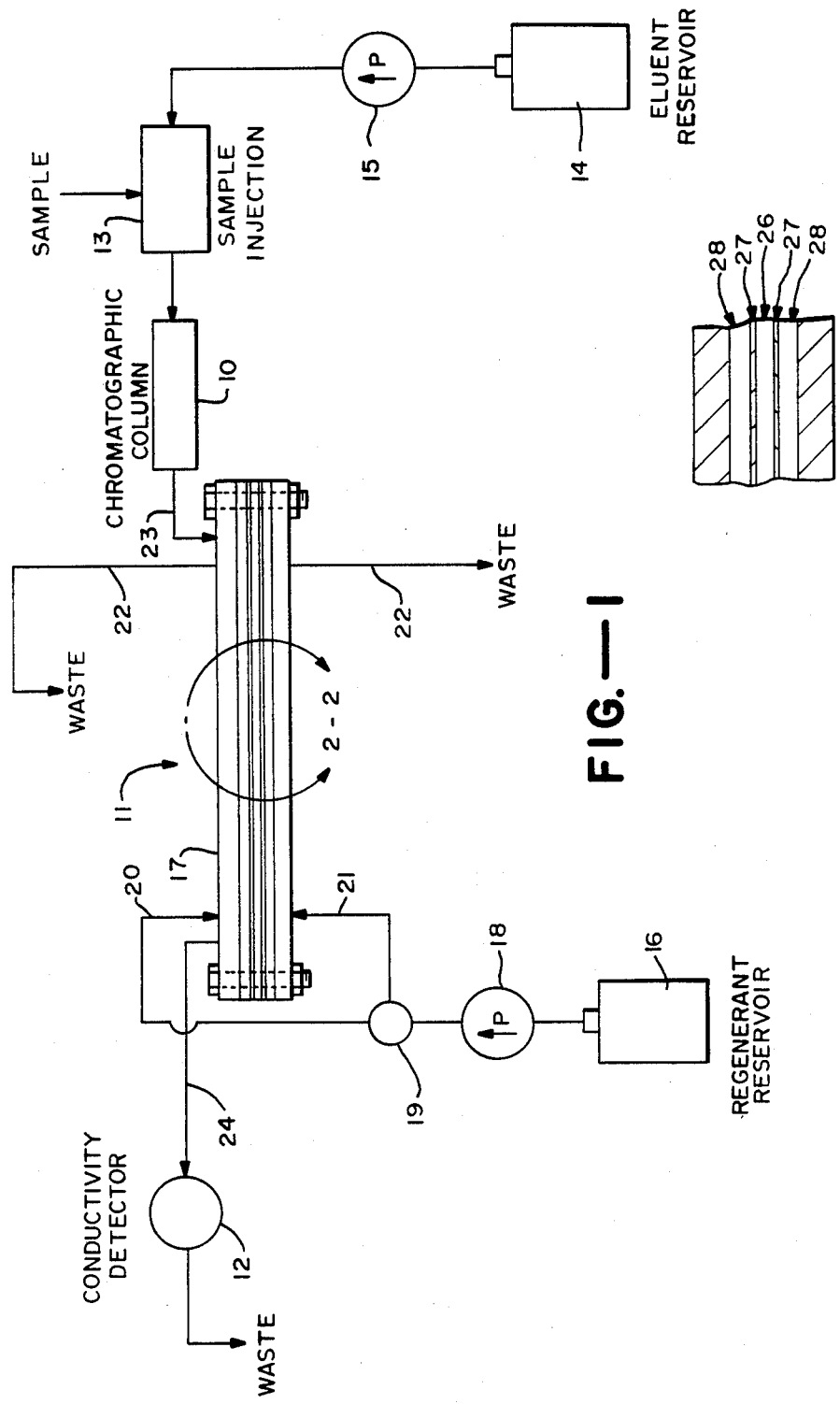

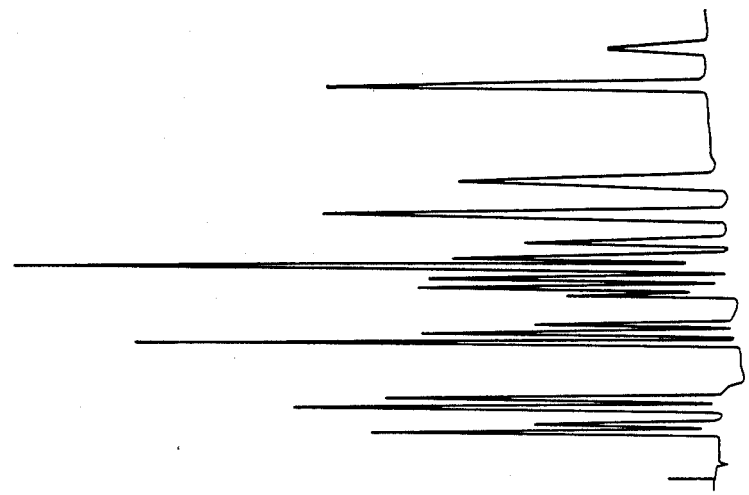
FIG.—4
FIG.—3

METHOD FOR BALANCING BACKGROUND CONDUCTIVITY FOR ION CHROMATOGRAPHY

CROSS-REFERENCE TO RELATED APPLICATIONS

Reference is made to copending application U.S. Ser. No. 658,148, filed Oct. 4, 1984 now abandoned and application U.S. Ser. No. 837,330, filed Mar. 3, 1986.

BACKGROUND OF THE INVENTION

The present invention relates to a method for balancing background conductivity in the analysis of anions in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the ion chromatographic separation stage, ions of an injected sample are eluted through a separation column using an electrolyte eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,956,559.

Suppression or stripping of the electrolyte is described in the above prior art references by an ion exchange resin bed. A different form of suppressor column is described in U.S. Pat. No. 4,474,664, in which a charged membrane in the form of a fiber or sheet is used in place of the resin bed. In sheet form, the sample and eluent are passed on one side of the sheet with a flowing regenerant on the other side of the sheet. The sheet comprises an ion exchange membrane partitioning the regenerant from the effluent of chromatographic separation. The membrane passes ions of the same charge as the exchangeable ions of the membrane to convert the electrolyte of the eluent to weakly ionized form, followed by detection of the ions.

In a typical commercial suppressor, a small amount of electrolyte passes in the effluent to the ion conductivity detector as background. Of course, such background conductivity is relatively low in comparison to the level of conductivity which would pass to the detector without use of the suppressor. However, the background conductivity can cause problems for an eluent of the gradient type wherein the concentration of electrolyte is progressively increased during the run. In such instances, the baseline of a chromatogram reflecting such background correspondingly increases adding difficulty in analyzing the chromatographic peaks. Sometimes, the background causes the baseline to go off-scale. It would be desirable to provide a way to maintain relatively constant baseline background conductivity during a gradient eluent run.

It is further known that boric acid, while a weak acid by itself, in the presence of polyhydroxy compounds such as glycerol or mannitol, acts as a much stronger acid. The boric acid and polyhydroxy compounds form a highly ionized complex. A binary composite solution of these type of compounds has been suggested for use as the eluent for analysis of anions in Miyanaga et al. U.S. Pat. No. 4,500,431.

SUMMARY OF THE INVENTION

In accordance with the invention, a method has been provided for balancing the background conductivity in an ion chromatography system using a gradient eluent with a progressively increasing concentration of electrolyte. It is particularly useful when the system includes a suppressor of the membrane type. In this system, a non-ionic counterbalancing precursor, preferably a polyhydroxy compound, e.g., mannitol, is pumped with the gradient eluent. As the electrolyte concentration increases during a run, the precursor concentration correspondingly decreases. Since the precursor is non-ionic, it does not affect separation of the ions in the chromatographic column.

The effluent from the chromatographic column is flowed through a conductivity detector for detection of the separated anions. Prior to passage into the conductivity detector, a complexing agent, preferably boric acid, is added to the effluent. Such complexing agent is of a type which reacts with the counterbalancing precursor to form a highly ionized complex at an ion concentration counterbalancing the increasing background concentration of the electrolyte flowing through the conductivity detector during the run to stabilize the level of background ion concentration.

If a membrane suppressor is used, the complexing agent is of a type which passes through the membrane. For this purpose, assuming the complexing agent to be an acid, it is preferable that it be non-ionic or weakly ionized so that it may pass through a cation membrane which is used in the detection of anions.

One advantage of the above system is that the same gradient pump for the gradient electrolyte also is used for the counterbalancing precursor. Also, the pump for the regenerant, typically of a non-gradient type can also be used for the complexing agent since it may be supplied at a constant concentration.

BRIEF DESCRIPTION OF THE DRAWINGS

FIG. 1 is a schematic view of apparatus for performing ion chromatography in accordance with the present invention.

FIG. 2 is a schematic expanded view of a portion of the suppressor of FIG. 1 taken at 2—2.

FIG. 3 is a chromatogram illustrating the baseline shift of conventional ion chromatography.

FIG. 4 is a chromatogram illustrating the baseline stability provided by the present invention.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

The purpose of the suppressor stage is to reduce the conductivity and noise of the analysis stream background while enhancing the conductivity of the analytes (i.e., increasing the signal/noise ratio), while maintaining chromatographic efficiency. Thus, the following parameters bear upon the performance of the suppressor: (1) dynamic capacity of suppression, measured as $\mu$Eq./min of eluent for each device; (2) background conductivity measured as $\mu$S/cm per device, and (3) chromatographic efficiency measured as a width at half height for flow injection or 5.5 (retention time/width at half height)[2] for the species retained in a separator.

The term "efficiency" describes the chromatographic properties in terms of the maintenance of the narrowness of the analyte bands that elute from the separator. On the other hand, "capacity" describes in quantitative terms the concentration of eluent that can be suppressed per unit time.

Referring to FIG. 1, a simplified apparatus for performing the present invention is illustrated. The system includes chromatographic separation means, typically in the form of a chromatographic column 10 which is packed with a chromatographic separation medium. In one embodiment referred to above, such medium is in the form of ion-exchange resin. In another embodiment, the separation medium is a porous hydrophobic chromatographic resin with essentially no permanently attached ion-exchange sites. This system is used for mobile phase ion chromatography (MPIC) as described in U.S. Pat. No. 4,265,634. An ion exchange site-forming compound, including hydrophobic portion and an ion-exchange site, is passed through the column and is reversibly absorbed to the resin to create ion-exchange sites.

Arranged in series with column 10 is suppressor means 11 serving to suppress the conductivity of the electrolyte of the eluent from column 10 but not the conductivity of the separated ions. The conductivity of the separated ions is usually enhanced in the suppression process.

The effluent from suppressor means 11 is directed to a detector in the form of conductivity cell 12 for detecting all the resolved ionic species therefrom, preferably in the form of a flow-through conductivity cell. A suitable sample is supplied through sample injection valve 13 which is passed through the apparatus in the solution of eluent from eluent reservoir 14 drawn by pump 15, of the gradient type, and then pass through the sample injection valve 13. The solution leaving column 10 is directed to suppressor means 11 wherein the electrolyte is converted to a weakly conducting form. The effluent with separated ionic species is then treated by suppressor means 11 and pass through conductivity cell 12.

In conductivity cell 12, the presence of ionic species produces an electrical signal proportional to the amount of ionic material. Such signal is typically directed from the cell 12 to a conductivity meter, not shown, thus permitting detection of the concentration of separated ionic species.

Suppressor means 11 includes a regenerant reservoir 16 or other source of regenerant solution which is directed to at least one flow-through regenerant channel in ion-exchange membrane device 17. Regenerant from reservoir 16 flows through a chromatographic pump 18 and a splitter valve 19 which separates the regenerant into two different conduits 20 and 21 to supply the regenerant to the regenerant flow-through passages and then to waste through conduit 22. Alternatively, the regenerant flows through the regenerant chambers sequentially then to waste. The effluent flows from chromatographic column 10 to membrane device 17 through conduit 23, and from the membrane device to the conductivity detector through conduit 24.

A preferred suppressor device is in the form of a sandwich suppressor including a central effluent chamber 26 defined on both sides by membranes 27 to the exterior of which are two regenerant flow channels 28. Such system preferably includes screens or the like, not shown, and is fully described in U.S. Ser. No. 658,148, filed Oct. 4, 1984 now abandoned, and application U.S. Ser. No. 837,330, filed Mar. 3, 1986.

In one mode of operation of the suppressor device 17, effluent from chromatographic column 10 is directed through the effluent flow channel 26 bounded on both sides by ion-exchange membranes 27 partitioning the regenerant from the effluent. The regenerant flows through the regenerant channels 28. The membranes 27 are preferentially permeable to ions of the same charge as the exchangeable ions of the membrane and resists permeation of ions of opposite charge. The exchangeable ions of the membrane are in the ion form necessary to convert the electrolyte of the eluent to a weakly ionized form. For maximum capacity, the regenerant flow is countercurrent to the effluent flow. The effluent from chromatographic column 10 is passed through the effluent flow channel 26 and contacts both membranes. The membranes are simultaneously contacted on their outer sides with the regenerant flowing in the opposite direction through the regenerant flow channels 28 so that the membrane forms a permselective partition between the regenerant and the effluent. Ions extracted from the effluent at the active ion-exchange sites of the membranes are diffused through the membranes and are exchanged with ions of the regenerant, and thus diffused ultimately into the regenerant. Application of a potential across the electrodes increases the mobility of the ions across the membrane. The resolved ionic species in the effluent leaving the suppressor device are detected with a conductivity detector.

For a system used to separate anions, the ion exchange membrane includes cation exchange cites and so is substantially impermeable to high ionized anions but permits the passage of the relatively unionized borate ion. A suitable membrane of this type is Raipore R-1010, as used in the suppressor sold by Dionex Corporation under the brand name Anion Micro Membrane Suppressor (AMMS).

Suitable eluents for use in the present invention include electrolytes such as the anionic dissociated forms of phenol and other substituted phenols such as p-cyanophenol, carbonate, and amino acids. Suitable concentations of electrolyte range from 0.1 mM to 100 mM. Suitable flow rates are 0.2–4 mL/min.

Suitable regenerant solutions include strong acids such as sulfuric acid. Suitable concentrations are from 5 mN to 70 mN. Suitable flow rates are from 1 to 15 mL/min.

Referring to a system for separating anions using a membrane suppressor of the foregoing type, it is preferable to include a counterbalancing precursor which is substantially non-ionic during passage through chromatographic column 10 so that it does not interfere with the chromatographic separation. Conversely, to be effective, it must be converted to a highly ionized form prior to passing through conductivity detector 12. It has been found that polyhydroxyl compounds, which are non-ionic while passing through the chromatographic column, complex with boric acid to form a highly ionized complex with boric acid. Thus, by adding boric acid to the effluent from the chromatographic column prior to passing through the conductivity detector, significant improvement in the background conductivity stability may be achieved.

In gradient elution, the eluent electrolyte concentration begins low and then is increased during the run. In this manner, weakly retained ions are separated and eluted first, and as the eluent concentration is increased, the more strongly retained ions are eluted.

The principle of balancing the baseline conductivity is by counterbalancing the increase in background conductivity due to the increases in concentration of the gradient electrolyte. This is accomplished by passing an ionized composition at a concentration opposed to that of the increasing concentration of electroylte in the eluent. Specifically, when the electrolyte in the eluent is at its lowest concentration at the beginning of the run, the complex is at its highest concentration, whereas when the eluent electrolyte is at its highest concentration at the end of the run, the counterbalancing complex is at its lowest concentration. The concentrations of the eluent electrolyte and of the complex are correspondingly selected to maintain a relatively constant background conductivity flowing through the conductivity detector. This selection takes into account the relative ionization of the complex and electrolyte and the corresponding ion concentration of the electrolyte from the start to the finish of the run.

When using the membrane suppressor, a typical regenerant solution is dilute sulphuric acid (e.g., 0.0025 to 0.035 moles). In that environment, boric acid will be relatively non-ionized due to its weak dissociation constant (pKa-9.14). Although excess boric acid will diffuse through the cation exchange membrane, it will have little effect in the regenerant because it is only weakly ionized. However, the boric acid anion serves as a complexing agent which passes through the membrane into the effluent stream to react with the polyhyroxy compound, specifically mannitol, and form a substantially stronger acid complex.

The concentration of the counterbalancing precursor (mannitol) will control, the ion concentration contributed by the complex. This permits the use of progressively decreasing concentrations of mannitol adjusted by one gradient pump 15 used for correspondingly increasing concentrations of electrolyte. Also, the boric acid may be pumped from regenerant reservoir 16 through constant flow pump 18, while accomplishing the desired gradient complex of decreasing ion concentration flowing through the conductivity detector. In this manner, existing ion chromatographs, such as Dionex Model 4,000i, with its gradient eluent pump and constant pressure regenerant pump may be used according to the present invention without additional pumps.

A suitable concentration of precusor is about 1 to 100 mM, at a ratio of 100 to 0.01 of the ion concentration of the eluent.

Suitable polyhydroxy compounds include sugars, preferably mannitol or glucose, or polyhydroxy alcohol, such as glycerol. A particularly effective compound is mannitol. It is neutral with typical pH levels of elution (from about 6 to 13) and so it can be added to the eluent without causing any changes in the separation of the anions. Preferably, the ratio of polyhydroxy compound to precursor ranges from about 0.1 to 0.5.

A typical gradient buffer at the beginning of the run is composed of p-cyanophenol, ammonia, and acetonitrile in deionized water. P-cyanophenol is a weak acid (PKA 8.0) and ammonia is a weak base (PKB 4.7), the solution is largely converted to ammonium p-cyanophenate, with excess ammonia. The purpose of the acetonitrile is to increase the solubility of P-cyanophenol and to prevent its absorption on the resin.

Although the eluent electrolyte concentration increases with time, the program may not be linear. Instead, it may contain linear sections as well as sections in which the concentration is held at a fixed value for a time, or is stepped to a high value. The purpose of this more complex program is to place the elution time of each ion in a manner which minimizes coelution.

While the membrane suppressor system of FIG. 1 is the preferred environment for use of the method of balancing baseline conductivity of the present invention, it should be understood that it is also applicable to other forms of suppressor such as of the ion exchange bed type. In that instance, the complexing agent could be pumped to the effluent after passing through the chromatographic column, and before or after passing through the suppressor bed into the conductivity detector. Yet another possible approach in a specialized system, with or without suppressor means between the chromatographic column and the conductivity detector, the complexing agent may likewise be pumped independently to the effluent after the chromatography column and before the conductivity detector.

In order to illustrate the present invention, the following samples of its practice are provided.

EXAMPLE 1

(Comparative example). This Example illustrates an ion chromatography run using a Dionex HPIC-AS6 anion separator column. The resin in the column is composed of styrene-divinylbenzene beads functionalized with quaternary ammonium groups. Anions are retained on the positively charged ammonium groups and eluted by p-cyanophenate anion. The sample includes the following seventeen anions: fluoride, 5 PPM; acetic formatic, 50 PPM; pyruvic, 5 PPM; chloride, 10 PPM; nitrite, 10 PPM; phosphate, 30 PPM; glutaric, 50 PPM; succinic, 50 PPM; maleic, 50 PPM; sulfate, 30 PPM; nitrate, 20 PPM; oxalic, 30 PPM; fumaric, 50 PPM; oxalacetic, 100 PPM; citric, 100 PPM; and isocitric, 100 PPM. For the chromatogram shown in FIG. 3, the p-cyanophenate eluent concentration program is not linear with time, but contains linear sections as well as sections in which the concentration is held at a fixed value for a time, or is stepped to a higher value.

The gradient program used in the chromatogram of FIG. 2 is as follows:

|  | Time since injection (min): | | | | | |
| --- | --- | --- | --- | --- | --- | --- |
|  | 0 | 3.0 | 3.1 | 7.0 | 13 | 15 |
| % of stock eluent: | 7 | 15 | 30 | 53 | 53 | 100 |

The stock eluent solution (35 mM p-cyanophenol, 50 mM ammonia, and 2% acetonitrile) begins at 7% mixed with the remainder of eluent (2% acetonitrile in deionized water) at a flow rate of 2.0 mL/min. The stock solution is linearly increased to 15% by 3.0 min. It is then stepped to 30% by 3.1 min., and then linearly increased to 53% at 7 min. This concentration is constant until 13 min., and then increased to 100% at 15 min., and remains constant for the rest of the run.

The effluent is then passed through a membrane suppressor (Dionex type AMMS). The regenerant solution comprises 25 mN $H_2SO_4$ at a flow rate of 10 mL/min.

The peaks shown in FIG. 3 are the 17 anions in the order listed in this example reading from left to right in the Figure. The sloping baseline in the chromatogram can interfere with anion determinations. In extreme cases, such unstable baselines can cause the peaks to go off scale.

EXAMPLE 2

In this Example, the same eluent system is used with the exception that mannitol was added to the eluent reservoir and boric acid was added to the regenerant stream. A stock solution of mannitol is prepared containing 50 mM mannitol and mixed with the eluent in accordance with the following program:

|  | Time since injection (min): | | | | | |
| --- | --- | --- | --- | --- | --- | --- |
|  | 0 | 3.0 | 3.1 | 7.0 | 13 | 15 |
| % of stock eluent: | 7 | 15 | 30 | 53 | 53 | 100 |
| % of mannitol stock: | 45 | 40 | 40 | 30 | 25 | 0 |

200 mM boric acid is added to the 25 mM sulfuric acid regenerant. In the suppressor, boric acid is neutral and diffuses through the cation exchange suppressor membranes. It then reacts with mannitol producing a stronger acid and some conductivity. The mannitol concentration is decreased during the run such that its conductivity decrease is matched by the increasing conductivity of the suppressed p-cyanophenol eluent.

The stable baseline conductivity in the conductivity detector is illustrated in FIG. 4 with the anion peaks in the same order as shown in FIG. 3.

I claim:

1. A method of ion chromatography with improved background conductivity stability for analyzing a sample solution containing a plurality of anions and using a gradient eluent, said method comprising
   (a) flowing said anion solution and a gradient eluent having an electrolyte of increasing ion concentration with time through a chromatographic column to separate said anions upon elution therefrom in an effluent, said gradient eluent further including an essentially non-ionic counterbalancing precursor at a concentration which decreases as the ion concentration of said electrolyte increases,
   (b) adding a complexing agent to said effluent from step (a) said complexing agent reacting with said counterbalancing precursor to form an ionized complex at an ion concentration counterbalancing increasing background ion concentration of said electrolyte flowing through said conductivity detector to thereby improve the stability of the level of background conductivity flowing through the conductivity detector, and
   (c) thereafter flowing said effluent through a conductivity detector to detect the separated anions, at least a portion of said electrolyte passing through said conductivity detector as increasing background ion concentraion with time corresponding to the increasing ion concentration of said electrolyte flowing in step (a).

2. The method of claim 1 in which said counterbalancing precursor comprises a polyhydroxy compound.

3. The method of claim 2 in which said polyhydroxy compound is selected from the group consisting of a sugar and a glycerol.

4. The method of claim 3 in which said sugar is selected from the group consisting of mannitol and glucose.

5. The method of claim 1 in which said complexing agent comprises boric acid.

6. The method of claim 1 further comprising, prior to step (c), the step of
   (d) passing the effluent from said chromatography column through suppressor means which permits passage of only background amounts of said electrolyte in ionized form, but which permits passage of said separated anions.

7. The method of claim 6 in which said complexing agent is added to said effluent after passage through said suppressor means.

* * * * *